United States Patent [19]

Schultz

[11] Patent Number: 5,298,409
[45] Date of Patent: * Mar. 29, 1994

[54] ANTIBODY-ENHANCED STEREOSPECIFIC HYDROLYSES

[75] Inventor: Peter G. Schultz, Oakland, Calif.

[73] Assignee: The Regents of the University of California, Oakland, Calif.

[*] Notice: The portion of the term of this patent subsequent to Mar. 2, 2010 has been disclaimed.

[21] Appl. No.: 989,450

[22] Filed: Dec. 11, 1992

Related U.S. Application Data

[63] Continuation of Ser. No. 574,674, Aug. 29, 1990, Pat. No. 5,190,865, which is a continuation-in-part of Ser. No. 383,465, Jul. 19, 1989, abandoned, which is a continuation-in-part of Ser. No. 273,455, Nov. 18, 1988, abandoned.

[51] Int. Cl.$^5$ .......................... C12P 13/00; C12P 7/62
[52] U.S. Cl. .................................... 435/106; 435/108; 435/128; 435/135; 435/188.5; 435/280
[58] Field of Search ...................... 435/108, 188.5, 280, 435/128, 135, 106; 530/388.9, 389.8

[56] References Cited

U.S. PATENT DOCUMENTS 4,888,281  12/1989  Schochetman et al. ............... 435/72
4,900,674   2/1990  Benkovic et al. ..................... 435/232

OTHER PUBLICATIONS

Lerner, R. A., et al., "Principles of Antibody Catalysis", *BioEssays* 9:102-112 (Oct. 1988).
Massey, R. J., "Catalytic antibodies catching on," *Nature* 328(6129):457-458 (Jul. 30, 1987).
*Webster's II New Riverside University Dictionary*, "enzyme," p. 437 (1984).
*Hackh's Chemical Dictionary*, "enzyme(s)," p. 242 (1969).
Janda, K. D., et al., "Catalytic Antibodies with Lipase Activity and R or S Substrate Selectivity," *Science* 244:437-440 (Apr. 28, 1989).
Benkovic, S. J., et al., "Catalysis of a stereospecific bimolecular amide synthesis by an antibody," *Proc. Natl. Acad. Sci. USA* 85:5355-5358 (Aug. 1988).
Pollack, S. J., et al., "Stereospecific Hydrolysis of Alkyl Esters by Antibodies," *J. Am. Chem. Soc.* 111:5961-5962 (1989).
Schultz, P. G., et al., "Catalytic Antibodies," *Chemical and Engineering News*, pp. 26-40 (May 28, 1990).
Nishino, N., et al., "*Pseudomonas aeruginosa* Elastase," *J. Biol. Chem.* 255(8):3482-3486 (1980).
Brown, J. M., et al., "Chemical asymmetric synthesis,"'*Nature* 342:631-636 (Dec. 7, 1989).
Whitesides, G. M., et al., "Enzymes as Catalysts in Synthetic Organic Chemistry", *Angew. Chem. Int. Ed. Engl.* 24:617-638 (1985).
Pollack, S. J., et al., "Selective Chemical Catalysis by an Antibody," *Science* 234:1570-1573 (Dec. 19, 1986).
Jacobs, J., et al., "Catalytic Antibodies," *J. Am. Chem. Soc.* 109(7):2174-2176 (1987).

(List continued on next page.)

*Primary Examiner*—Charles L. Patterson, Jr.
*Attorney, Agent, or Firm*—Townsend and Townsend Khourie and Crew

[57] ABSTRACT

Hydrolyses of various chiral compounds are performed in stereospecific manner by antibodies generated from analogs of transition states of the compounds. The compounds susceptible to such hydrolysis include esters, thioesters and amides. In certain embodiments of the invention, antibodies with a strong selectivity toward one of the two enantiomers with respect to the chiral substrate are generated from haptens which is a mixture of enantiomers. A method of screening antibodies thus generated for those which are active towards the desired cleavage is also disclosed, using a test compound similar in structure to the intended substrate but which contains both a fluorescence donor group and a fluorescence quenching group, situated on opposite sides of the cleavage site. Cleavage by active antibodies results in separation of the groups and a resulting termination of the quenching effect.

17 Claims, No Drawings

OTHER PUBLICATIONS

Tramontano, A., et al., "Catalytic Antibodies", *Science* 234:1566–1569 (Dec. 19, 1986).

Cochran, A. G., et al., "Photosensitized Cleavage of a Thymine Dimer by an Antibody," *J. Am. Chem. Soc.* 110:7888–7890 (1988).

Shokat, K. M., et al., "A new strategy for the generation of catalytic antibodies," *Nature* 338:269–271 (Mar. 16, 1989).

Shokat, K. M., et al., *Angew. Chem., Int. Ed. Engl.* 100:1227–1229 (1988).

Iverson, B. L., et al., "Sequence Specific Peptide Cleavage Catalyzed by an Antibody," *Science* 243:1184–1188 (Mar. 3, 1989).

Pollack, S. J., et al., "Introduction of Nucleophiles and Spectroscopic Probes into Antibody Combining Sites", *Science* 242:1038–1040 (Nov. 18, 1988).

Pollack, S. J., et al., "A Semisynthetic Catalytic Antibody," *J. Am. chem. Soc.* 111:1929–1931 (1989).

Napper, A. D., et al., "A Stereospecific Cyclization Catalyzed by an Antibody," *Science* 237:1041–1043 (Aug. 28, 1987).

Jackson, D. Y., et al., "An Antibody-Catalyzed Claisen Rearrangement," *J. Am. Chem. Soc.* 110:4841–4842 (1988).

Hilvert, D., et al., "Catalysis of concerted reactions by antibodies: The Claisen rearrangement," *Proc. Natl. Acad. Sci. USA* 85:4953–4955 (Jul. 1988).

Schechter, I., et al., "Preferential Formation of Antibodies Specific toward D-Amino Acid Residues upon Immunization with Poly-DL-peptidyl Proteins," *Biochemistry* 6(3):897–905 (Mar. 1967).

ANTIBODY-ENHANCED STEREOSPECIFIC HYDROLYSES

This invention was made with Government support under Grant Contract No. AI-24695, awarded by the Department of Health and Human Services, and under Grant Contract No. N00014-87-K-0256, awarded by the Office of Naval Research. The Government has certain rights in this invention.

This is a continuation of application Ser. No. 07/574,674, filed Aug. 29, 1990 now U.S. Pat. No. 5,190,865, which is a continuation-in-part of application Ser. No. 07/383,465, filed Jul. 19, 1989 (now abandoned), which is a continuation-in-part of application Ser. No. 07/273,455, filed Nov. 18, 1988 (now abandoned).

BACKGROUND OF THE INVENTION

Enzymes are playing an increasingly important role as catalysts in chemistry, due to their ability to catalyze highly selective transformations of chiral or polyfunctional molecules. See Whitesides, G. M., et al., *Agnew. Chem., Int. Ed. Engl.* 24:617 (1985). Many reactions exist for which enzymes are unavailable, however. To address this situation, Pollack, S. J., et al., *Science* 234:1570 (1986), Jacobs, J. W., et al., *J. Am. Chem. Soc.* 109:2174 (1987), and Tramontano, A., et al., *Science* 234:1566 (1986) have demonstrated that the high binding specificity of the immune system can be exploited to develop new biological catalysts with tailored specificities. In addition, antibodies generated with catalytic groups in the binding site have been reported by Cochran, A. G., et al., *J. Am. Chem. Soc.* 110:7888 (1988), and Shokat, K. M., et al., *Nature London)* 338:269 (1989); the generation of antibodies with cofactor binding sites has been reported by Shokat, K. M., et al., *Agnew. Chem., Int. Ed. Engl.* 100:1227 (1988), and Iverson, B. L., et al., *Science* 243:1184 (1989); the generation of semisynthetic antibodies has been reported by Pollack, S. J., et al., *Science* 242:1038 (1988), and Pollack, et al., *J. Am. Chem. Soc.* 111:1929 (1989): use of the notion of approximation in the generation of antibodies has been reported by Napper, A. D., et al., *Science* 237:1041 (1987); and the notion of transition state stabilization as applied to the generation of antibodies has been reported by Pollack, S. J., et al., *Science* 34:1570 (1986), Jacobs, J. W., et al., *J. Am. Chem. Soc.* 09:2174 (1987), Tramontano, A., et al., *Science* 234:1566 (1986), Jackson, D. Y., et al., J. Am. Chem. Soc. 110:4841 (1988), and Hilvert, D., et al., *Proc. Natl. Acad. Sci. U.S.A.* 85:4953 (1988). The experimental data in the examples in this specification was published in Pollack, S. J., et al., *J. Am. Chem. Soc.* 111:5961 (1989).

The notion of transition state stabilization as applied to hydrolysis of esters has been reported by Janda, K. D., et al., *Science* 244:437 (1989), whose work has involved the generation of catalytic antibodies which stereospecifically hydrolyze unactivated esters of chiral alcohols. Other literature of potential relevance to this invention is that of Schechter, I., et al., Biochemistry 6:897 (1967), pertaining to the greater immunogenicity of D amino acids and their analogs as compared to the L counterparts.

A disclosure of a cleavage reaction which involves separation of a fluorescence-generating 2-aminobenzoyl group from a fluorescence-quenching 4-nitrobenzylamide group originally present on the same molecule, and the increase in fluorescence which results, is offered by Nishino, N., et al., *J. Biol. Chem.* 255:3482 (1980).

SUMMARY OF THE INVENTION

It has now been discovered that stereospecific hydrolysis can be performed on certain additional classes of compounds, using antibodies generated from appropriate transition state analogs. These classes are as follows:

(a) chiral esters in which the chiral center is on the acid portion;

(b) chiral thioesters in the chiral center is on either the acid portion or the thiol portion; and (c) chiral amides in which the chiral center is on either the acid portion or the amine portion.

Associated with the first class (chiral esters in which the chiral center is on the acid portion) is the discovery of an unexpected selectivity in the generation of antibody from a mixture of enantiomeric antigens: while both enantiomers in the mixture are theoretically capable of eliciting antibodies, a strong selectivity toward antibodies specific to one of the two enantiomers is demonstrated. Thus, by the practice of the present invention, a mixture of enantiomeric antigens representing hydrolysis transition state analogs of the ester can be used to elicit antibodies specific for only one of the enantiomers. The antibodies, either as a polyclonal mixture or as monoclonals, can then be used to selectively hydrolyze the ester from a mixture of enantiomers of the ester to a single enantiomer of the carboxylic acid.

Preferential antibody generation also occurs in the remaining classes. For each class, however, isolated antibodies specific for only one enantiomer, or antibody combinations in which all are of the same idiotype specific for that enantiomer, will selectively catalyze the hydrolysis of the corresponding enantiomer of the substrate.

A further aspect of this invention is the discovery of a method of screening antibodies for catalytic cleavage activity utilizing fluorescence detection. According to this method, the candidate antibodies are tested on a test substrate which contains both a fluorogenic group and a fluorescence quenching group. The two groups are arranged on the substrate molecule such that when the cleavage occurs due to an active antibody, the two groups are separated by the cleavage. Due to the separation, the fluorescence quenching group is no longer capable of inactivating the fluorogenic group, and detectable fluorescence occurs.

DETAILED DESCRIPTION OF THE INVENTION AND PREFERRED EMBODIMENTS

The chiral esters and amides addressed by this invention extend to a wide range of structures. Substrates of particular interest for both esters and amides are those in which the chiral center is a carbon atom located at a distance of four atoms or less from the carbonyl carbon, with the intervening atoms, if any, being carbon atoms or a nitrogen, oxygen or sulfur atom (plus optionally carbon atoms in addition), depending on the substrate. Those bearing a chiral center at a distance of two atoms or less are more preferred. The most preferred ester substrate is

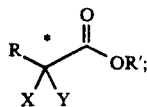

the most preferred thioester substrates are

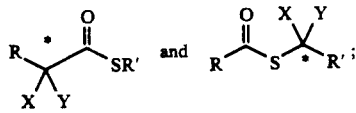

and the most preferred amide substrates are

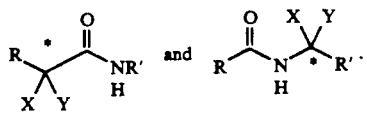

In these formulas, the chiral center is indicated by the asterisk, and the symbols R, R', X and Y represent miscellaneous substituents and substituent groups.

For ester and thioester substrates, further types of particular interest are esters and thioesters of aryl carboxylic acids, alkyl carboxylic acids, alicyclic carboxylic acids, and heterocyclic carboxylic acids. Still further types of particular interest are esters and thioesters of amino acids, including those in which the alcohol portion are alkyl and substituted alkyl alcohols and thiols. Still further esters of interest are peptide- and oligopeptide-substituted esters of amino acids. For amide substrates, the invention extends to those containing aryl, alkyl, alicyclic and/or heterocyclic groups bonded to either the carbonyl carbon or the nitrogen atom.

Substituents on any of these groups may vary widely. Notable examples are alkyl groups, aryl groups, further amino acids, halogens, heterocyclic groups, amino groups, and fused ring structures.

The invention is of particular interest in connection with the selective hydrolysis of one stereoisomer or enantiomer in a mixture of two or more such isomers. A notable combination for which the invention is particularly effective is that of D- and L-enantiomers of an amino acid ester.

Methods of eliciting antibodies for use in the present invention involve the use of a hapten designed to approximate the unstable transition state of the ester which decomposes into the acid and alcohol products of the hydrolysis. The preferred hapten is a stable analogue of the transition state, the analogue being one in which an unstable portion of the transition state has been replaced with a stable group of similar size, shape, orientation and electronic configuration. The analogue is a species which can be synthesized and isolated in high purity, unlike the unstable transition state which it mimics.

Since the transition state of an ester or an amide hydrolysis reaction is one in which the carbonyl carbon of the ester or amide assumes an unstable tetrahedral form, the hapten will be a species which approximates the size, shape, orientation and electronic configuration of the tetrahedral carbon, but is also stable. Various types of hapten meet this description. In some of these haptens, for example, the tetrahedral carbon is replaced with another atom, such as phosphorus or nitrogen, in a stable form approximating the tetrahedral carbon. In other haptens, that carbon is in the carbonyl form and a neighboring atom or atoms close to the carbonyl carbon are replaced with atoms which upon hydration cause the carbonyl carbon to convert to a stable tetrahedral form approximating the transition state. In still other haptens, the carbonyl carbon is replaced by a tetrahedral carbon atom with substituent(s) which render it stable while still approximating the transition state. In all cases, the haptens will contain appropriate substituents to provide the overall shape and electronic configuration desired. Preferred examples of haptens in which the tetrahedral carbon of the transition state is replaced by a non-carbon atom are phosphinates, phosphonates (including sulfur-substituted analogs), phosphonamidates and phosphoramidates, all of which contain the group

in which the P atom replaces the tetrahedral carbon atom of the transition state. In phosphinates, the two free bonds shown above each join the P atom to a carbon atom. In phosphonates, one of the free bonds is joined to a carbon atom and the other to an oxygen atom or, in the case of sulfur-substituted analogs, a sulfur atom. In phosphonamidates, one of the free bonds is joined to a carbon atom and the other to a nitrogen atom. In phosphoramidates, one of the free bonds is joined to an oxygen atom and the other to a nitrogen atom. Preferred phosphorus-containing haptens for ester hydrolysis are those containing either

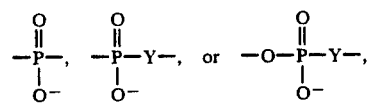

where Y is O or S, substituting for the —CO2 group to be hydrolyzed. Particularly preferred are those of the formula

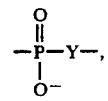

the most preferred of the latter being those in which Y is O.

Preferred phosphorus-containing haptens for thioester hydrolysis are those containing either

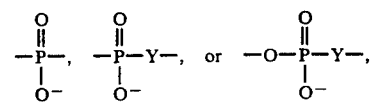

where Y is O or S, substituting for the —C(O)—S— group to be hydrolyzed. Particularly preferred are those of the formula

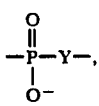

the most preferred of the latter being those in which Y is S.

Preferred phosphorus-containing haptens for amide hydrolysis are phosphonamidates and phosphoramidates containing the group

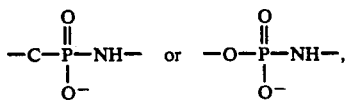

respectively, with the P atom at the position corresponding to that of the carbonyl carbon of the —C(O)—NH— group to be hydrolyzed.

Preferred examples of haptens in which the tetrahedral carbon is in the carbonyl form while neighboring atoms are replaced by other atoms are α-fluoroketones, i.e., those containing one of the following groups:

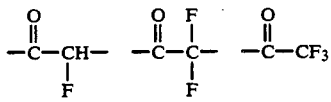

in which the carbonyl carbon is shown and the carbon atom to which the F atoms are bonded replaces the O, S, or N atoms in the esters, thioesters or amides, respectively. The third α-fluoroketone shown above (i.e., the trifluoromethylketone) differs from the first two by having only one bond for attachment of an adjacent group rather than a bond on each side. A hapten containing such a trifluoromethylketone group can therefore only mimic the acid moiety of the substrate, and will be useful in applications where the acid moiety is of primary importance.

A preferred example of a hapten in which the carbonyl carbon is replaced by a tetrahedral carbon atom is one containing a hydroxymethylene group

in place of the carbonyl group.

In preferred embodiments of the invention, a mixture of hapten enantiomers is used, with racemic mixtures or approximately equimolar mixtures of the enantiomers.

The use of the haptens in generating the antibodies follows conventional procedures involving host immunization. The haptens are generally coupled to carrier molecules which render them immunogenic, the coupling achieved through conventional linking groups or spacers. Further advantages in both quantity and specificity may be obtained by the use of monoclonal antibodies.

The terms "antibody" and "antibodies" as used herein are intended to include both whole antibodies and antibody fragments, such as polypeptide sequences taken from or identical to those present at antigen binding sites on naturally occurring or otherwise fully formed antibodies. The terms also include antibodies and antibody fragments made by recombinant DNA techniques, including single-chain constructs, as well as antibodies and antibody fragments which are conjugated to further species such as solid supports.

The hydrolysis reactions may be conducted in accordance with conventional techniques, although the antibodies will lessen or eliminate the need for other catalysts and in some cases permit the reaction to proceed under milder conditions than would otherwise be necessary for a beneficial yield at a practical reaction rate.

Turning next to the aspect of the invention whereby antibodies are screened for cleavage activity, central to this aspect of the invention is a test substrate which contains both a fluorescence energy donor group and a fluorescence energy quenching group, situated on opposite sides of the desired cleavage site. The test substrate is an analog of the substrate for which the cleavage reaction is intended, and is preferably identical to the intended substrate except for the presence of the donor and quenching groups (one or both of which may also be present on the intended substrate if desired). In preferred embodiments, these groups are covalently bonded to the test substrate and are sufficiently removed from the cleavage site that they will not interfere with antibody recognition of the substrate at the region of the cleavage site. Antibodies which are active as cleavage catalysts will thus recognize both the test substrate and the actual substrate sought to be cleaved (i.e., the substrates on whom the antibodies are intended for ultimate use). The groups will be sufficiently close to each other, however, that they will interact prior to cleavage, i.e., the quenching group will effectively reduce the emission of the donor group. Cleavage of the desired bond by catalytic activity of the antibody will result in separation of the donor and quenching groups, so that they reside individually on separate molecules rather than together on the same molecule.

This aspect of the invention is applicable to cleavage reactions in general. Preferred cleavage reactions are hydrolysis reactions, and of these, ester, thioester, amide, peptide and glycosidic bond hydrolysis reactions are the most preferred.

A wide variety of donor and quenching groups may be used. Examples of donor/quencher pairs are 2-aminobenzoyl/4-nitrobenzylamide, 6-methoxyquinoline/4-nitrobenzyl, tyrosin/tryptophan, naphthyl/dansyl, terbium tris(dipicolinate)/nitrobenzodiazyl (NBD), and 7-hydroxy-4-methylcoumarin/4-dimethylaminophenyl azophenyl.

The degree of difference in fluorescence emission which results from the cleavage reaction is not critical and may vary from one system to the next, within the scope of the invention. Any difference which is detectable within normal limits of detection will suffice. The most appropriate degree of difference for any particular system will vary with the assay procedure and the method of detection.

The protocol of the assay is also noncritical and may vary. The candidate antibodies will first be isolated from each other, and then, as one example, they may be placed either in individual solutions, or as another example, immobilized in discrete regions on a solid or semi-solid support, such as for example agar, glass or cellulose. The test substrate may also be used in liquid solution, or, alternatively, immobilized uniformly on the surface of a solid or semi-solid support, such as, for example, glass, cellulose, polystyrene or other polymeric material. The test substrate is then contacted with each antibody, either by adding the test substrate to the antibody solution, or in the case of antibodies immobilized on a support, contacting the support with a solution of the test substrate or with the support on which the test substrate is immobilized. After contact for sufficient time to permit any reaction capable of occurring to occur, the test substrate is washed by conventional procedures. Excitation and detection of the substrate are then conducted in accordance with standard procedures, and done in such a manner as to permit one to identify the antibodies associated with a fluorescence increase. Conventional equipment and procedures, such as the use of a spectrofluorimeter for solution phase measurements or a scanning fluorescence microscope for detecting immobilized fluorophores, may be used.

The following examples are offered for purposes of illustration, and are intended neither to limit nor to define the invention in any manner.

These examples illustrate the preparation of the hapten.

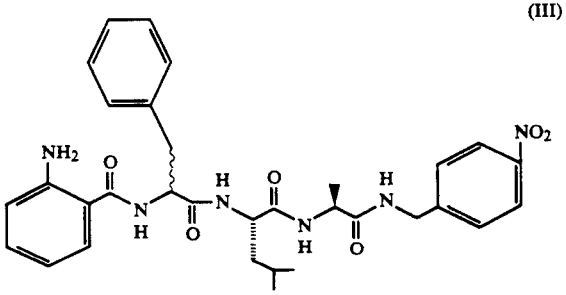

(III)

and Examples 4 and 5 illustrate the syntheses of two additional esters.

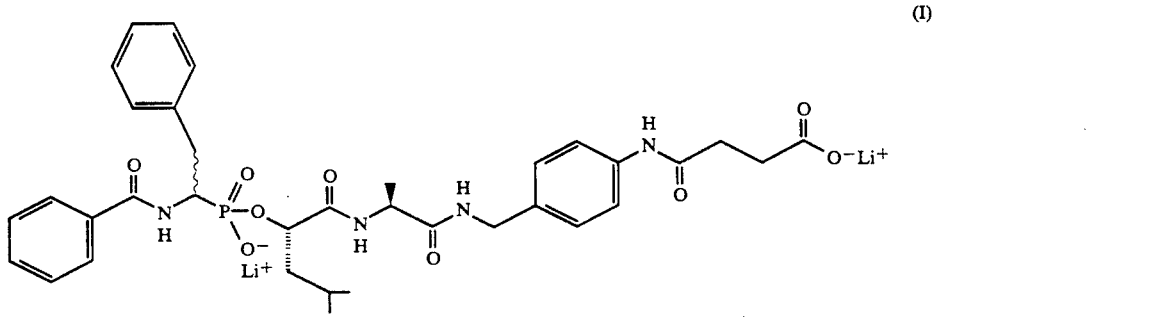

(I)

which is an analog of the transition state for the hydrolysis of the ester

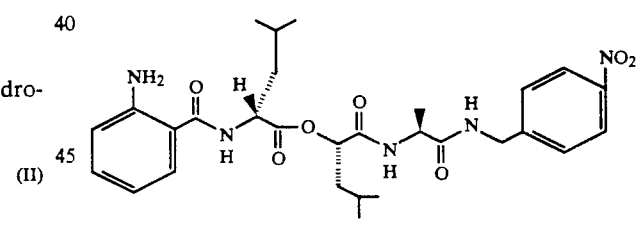

(II)

(IV)

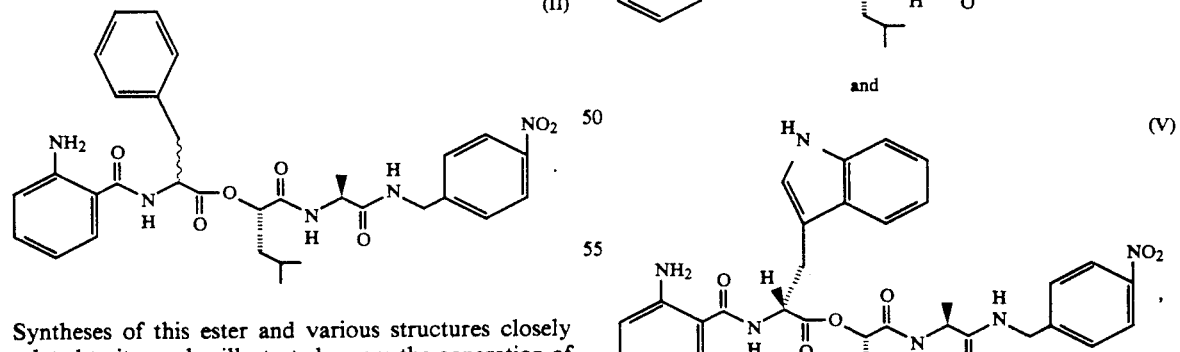

and (V)

Syntheses of this ester and various structures closely related to it are also illustrated, as are the generation of antibodies to the hapten, and attempts to use these antibodies as catalysts for the hydrolysis of the ester and its analogs.

Example 1 illustrates the synthesis of the hapten I as a roughly equimolar mixture of its two diastereomers. Following this is an illustration of the synthesis of the substrate II in Example 2, again as a roughly equimolar mixture of the substrate's two diastereomers. Example 3 illustrates the synthesis of a closely related tripeptide.

respectively, differing from the ester II by substituting different amino acids for the acid portion of the ester.

Following these examples are descriptions of the use of the hapten I in generating antibodies, and the use of the antibodies in attempts to accelerate the hydrolysis of the three esters II, IV and V and the tripeptide III.

EXAMPLE 1

Synthesis of Hapten I

A. Preparation of Succinic Acid Mono(N-t-Butoxycarbonyl 4-Aminomethyl)anilide Monomethyl Ester

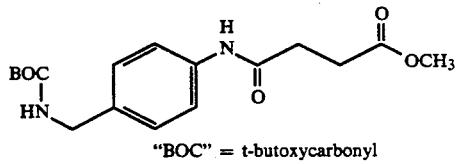

"BOC" = t-butoxycarbonyl

To a mixture of {N-(t-butoxycarbonyl)-4-aminomethyl}aniline (11.1 g, 50 mmol) and dry pyridine (12 mL, mmol) in dry dioxane (50 mL), held at room temperature under nitrogen, was added carbomethoxypropionyl chloride (6.5 mL, mmol), and the mixture was stirred for 12 h. A white precipitate was formed and removed, and the filtrate was concentrated in vacuo. The crude product was purified by silica gel chromatography with a 6×50 cm column, eluting with a gradient of 40% to 60% ethyl acetate in hexanes to give the product as a white solid (7.9 g, 23.5 mmol, 47% yield). Its structure was confirmed as that of succinic acid mono(N-t-butoxycarbonyl 4-aminomethyl)anilide monomethyl ester as follows:

melting point 120–121° C.;

IR (KBr pellet) 3305, 2985, 1730, 1670, 1601, 1532, 1430, 1366, 1170 cm$^{-1}$;

$^1$H-NMR (acetone-d$_6$) δ 1.40 (s, 9H), 2.64 (s, 4H), 3.61 (s, 3H), 4.19 (d, 2H, J=6.1), 7.20 (d, 2H, J=8.5), 7.57 (d, 2H, J=8.4), 9.20 (s, 1H);

mass spectrum (EI) 336 (M), 305, 279, 262, 248, 236, 230, 220, 203;

elemental analysis: calculated for $C_{17}H_{24}N_2O_5$: C, 60.71; H, 7.14; N, 8.33 found: C, 60.45; H, 7.13; N, 8.27.

B. Removal of N-t-Butoxycarbonyl Group with Trifluoroacetic Acid

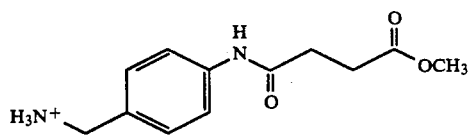

The t-butoxycarbonyl-protected compound of the preceding section (6.7 mmol) was dissolved in trifluoroacetic acid (TFA) (10 mL) and stirred under nitrogen at room temperature for 3h. The TFA was then removed in vacuo. Twice, ethyl acetate (10 mL) was added and removed in vacuo to remove residual TFA. The resulting residue was used directly in subsequent coupling reactions.

Preparation of (−)N-(L-2-Hydroxy-4-methylpentanoyl)-L-alanyl Aminobenzyl Derivative

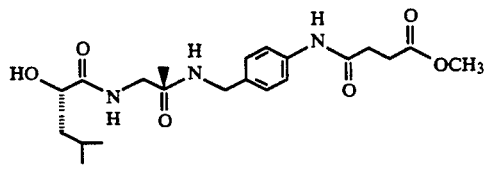

A mixture was prepared from the following:

(−)N-(L-2-hydroxy-4-methylpentanoyl)-L-alanine (1.36 g, 6.7 mmol), conveniently referred to as NHMPA, and whose formula is as follows

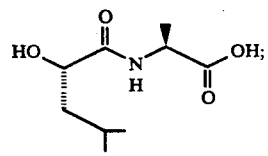

succinic acid mono(4-ammoniomethyl)anilide monomethyl ester, TFA salt (6.7 mmol) (from the preceding section of this Example);

hydroxybenzotriazole (0.90 g, 6.7 mmol); and triethylamine (2.8 mL, 20 mmol);

in dimethylformamide (10 mL) and methylene chloride (40 mL). To this mixture was added dicyclohexyl carbodiimide (DCC) (1.52 g, 7.4 mmol) under nitrogen at 0° C., and the mixture was stirred for 2h at 0° C. followed by 14h at room temperature. The dicyclohexyl urea (DCU) was filtered off and the filtrate was concentrated in vacuo. The residue was dissolved in ethyl acetate (100 mL) and more DCU was filtered off. The ethyl acetate was washed with water (4×20 mL), 3N HCl (20 mL), and saturated sodium bicarbonate (20 mL) and dried over MgSO$_4$. The product slowly crystallized from ethyl acetate as a white solid (1.35 g, 3.22 mmol, 48% yield). Its structure was identified as that of the title compound of this section by the following:

melting point 147°–148° C.;

IR (KBr pellet) 3300, 2975, 1730, 1665, 1640, 1630, 1550, 1530, 1415, 1260 cm$^{-1}$;

1H-NMR (acetone-d) δ 0.89 (d, 3H, J=6.5), 0.90 (d, 3H, J=6.6), 1.33 (m, 1H), 1.52 (m, 2H), 1.91 (d, 3H, J=7.0), 2.64 (s, 4H), 3.61 (s, 3H), 4.05 (m, 1H), 4.33 (d, 2H, J=6.0), 4.43 (m, 1H), 7.19 (d, 2H, J=8.5), 7.56 (d, 2H, J=8.5), 7.70 (s, 1H);

$^{13}$C-NMR (acetone-d$_6$) δ 19.2, 21.7, 23.8, 25.0, 31.9, 43.0, 44.4, 44.5, 49.0, 51.7, 70.9, 119.9, 128.9;

mass Spectrum (EI) 421 (M), 389, 374, 353, 333, 302, 276, 260, 235, 220, 203, 188, 175, 158;

elemental analysis: calculated for $C_{21}H_{31}N_3O_6$: C, 59.86; H, 7.36; N, 9.98. found: C, 59.99; H, 7.33; N, 9.81.

D. Preparation of Carbobenzoxy-protected Phosphonate Methyl Ester

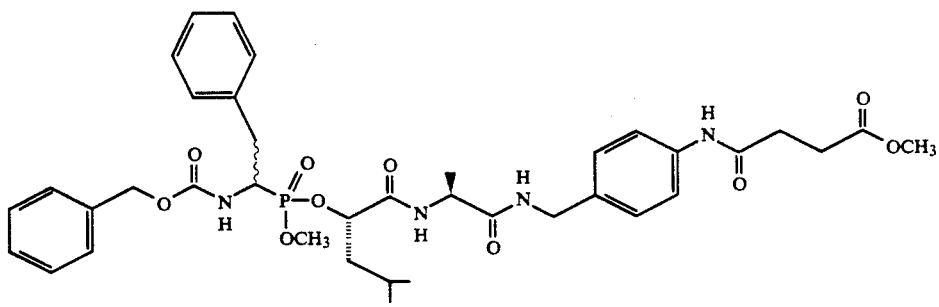

A solution of the following phosphonic acid

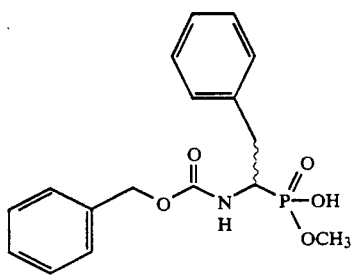

(1.05 g, 3.0 mmol) in dry, ethanol-free chloroform (10 mL) was treated with thionyl chloride (0.5 mL) and stirred for 3h under nitrogen at room temperature. The mixture was concentrated in vacuo to give the crude chloridate as an oil. This oil was dissolved in ethanol-free chloroform (10 mL) and cooled to 0° C.

The NHMPA from the preceding section of this Example (1.26 g, 3.0 mmol) was added, followed by dry pyridine (0.55 mL, mmol). The resulting mixture was stirred for 12h at 0° C. with gradual warming to room temperature, after which time the volatiles were completely removed in vacuo. Residual pyridine was azeotropically removed with toluene to give a tan solid. The crude product was purified by silica gel chromatography using a 5×40 cm column and eluting with a gradient of 2 to 5% methanol in methylene chloride to give an off-white crystalline solid (650 mg, 0.86 mmol, 29% yield) whose structure was identified as that of a mixture of diastereomers of the title compound by the following:

melting point 65°-67° C.;

IR (KBr pellet) 3290, 2960, 1730, 1660, 1600, 1530, 1410, 1250, 1060, 740, 700;

$^1$H-NMR (CDCl$_3$) δ 0.93 (d, 6 H, J=6.6), 1.37 (d, 3H, J=7.2), 1.5–1.8 (m, 3H), 2.64 (d, 2H, J=9.0), 2.66 (m, 2H), 2.70 (d, 2H, J=6.0), 3.59 (d, 3H, J=11.8), 3.67 (s, 3H), 4.33 (d, 2H, J=6.0), 4.45 (m, 1H), 4.77 (m, 1H), 5.00 (s, 2H), 4.55 (m, 1H), 7.19 (d, 2H, J=8.5), 7.25 (m, 10H), 7.42 (d, 2H, J=8.5 Hz), 8.65 (s, 1H);

$^{31}$P-NMR δ 25.6, 26.3, 26.5, 27.3;

mass spectrum (FAB+) 753 (MH+), 737, 619, 517, 404, 390, 372, 350, 310;

elemental analysis: calculated for C$_{38}$H$_{49}$N$_4$O$_{10}$P: C, 60.64; H, 6.52; N, 7.45; P, 4.12. found: C, 60.46; H, 6.39; N, 7.63; p, 3.86.

E. Conversion to N-Benzoxy-Protected Phosphonate Methyl Ester

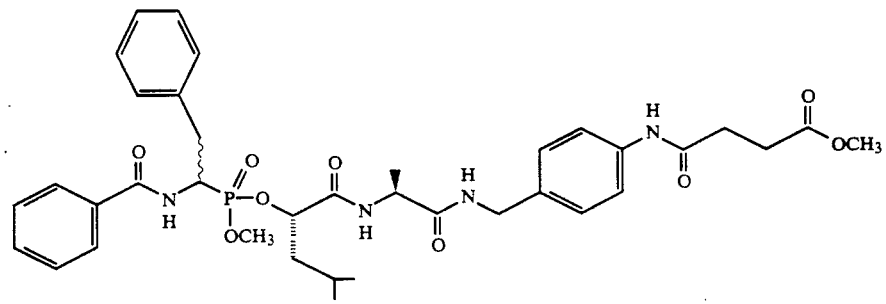

The carbobenzoxy-protected phosphonate of the preceding section of this Example (376 mg, 0.50 mmol) was dissolved in methanol (10 mL) and 4-toluenesulfonic acid (95 mg, 0.50 mmol) was added. The mixture was hydrogenolized at 1 atmosphere hydrogen for 2 days in the presence of 10% Pd on carbon (200 mg). The resulting mixture was filtered through celite and the solvent removed from the filtrate in vacuo. The resulting oil was dissolved in methylene chloride (6 mL) and cooled to 0° C. Benzoic anhydride (Fluka) (310 mg, 1.50 mmol) was added, followed by triethylamine (0.21 ml, 1.5 mmol). The mixture was stirred under nitrogen at 0° C. with gradual warming to room temperature. After 13h, the mixture was diluted with methylene chloride to 15 mL and washed with 1N HCl (2×10 mL) and saturated NaHCO$_3$ (2×10 mL). The mixture was then dried over MgSO$_4$, and the solvent was removed in vacuo to give a pale yellow oil. The crude product was purified by silica gel chromatography using a 2×30 cm column and eluting with a gradient from 2 to 5% methanol in methylene chloride to give a white crystalline solid (246 mg, 0.34 mmol, 68% yield), whose structure was identified as that of the formula shown above by the following:

melting point 73°-75° C.;

IR (KBr pellet) 3280, 2970, 1740, 1655, 1650, 1605, 1530;

$^1$H-NMR (CDCl$_3$) δ 0.93 (d, 6H, J=6.6), 1.37 (d, 3H, J=7.2), 1.5-1.8 Hz (m, 3H), 2.64 (d, 2H, J=9.0), 2.70 (d, 2H, J=6.0), 3.29 (m, 2H), 3.68 (s, 3H), 4.33 (d, 2H, J=6.0), 4.35 (m, 1H), 4.50 (m, 1H), 4.77 (m, 1H), 7.19 (d, 2H, J=8.5), 7.25 (m, 5H), 7.40 (m, 5H), 7.63 (d, 2H, J=8.5), 7.79 (m, 1H), 8.05 (m, 1H);

$^{31}$P-NMR δ 24.8, 26.0, 26.3, 27.1;

mass spectrum (FAB+) 723 (MH+), 707, 691, 661, 609, 487, 459, 406, 390, 342, 320, 302, 302, 288, 235, 220, 185;

elemental analysis: calculated for C$_{37}$H$_{47}$N$_4$O$_9$P: C, 61.50; H, 6.51; N, 7.76; P, 4.29. found: C, 61.83; H, 6.37; N, 7.72; P, 4.11.

F. Conversion to Phosphonate Hapten I

To the dimethyl ester prepared in the preceding example (144 mg, 0.20 mmol) was added a 0.6 M solution of lithium thiopropylate in hexamethylphosphoramide (HMPA) (2.0 mL) under argon and the mixture was stirred at room temperature under argon for 10h. Water (2 mL) was added and the mixture was washed with chloroform (5×1 mL) to remove the HMPA. The aqueous layer was applied to a 1.5 cm×25 cm column of DEAE Sephadex A25 (bicarbonate form) and eluted with a linear gradient of 500 mL of 0 to 0.5M triethylammonium bicarbonate, pH 8.6. The fractions containing the product as measured by A$_{257}$ were combined and lyophilized. The resulting solid was dissolved in water (2 mL) and applied to a 1.5 cm×25 cm column of Dowex 50W-8X cation exchange resin, lithium form. The A$_{257}$ fractions were combined and lyophilized to give a white crystalline solid (70 mg, 0.10 mmol, 50% yield), identified as the hapten I by the following:

melting point (270° C.);

IR (KBr pellet) 3650–3000, 1665, 1640, 1613, 1540, 1453, 1403, 1110;

$^1$H-NMR (D$_2$O) δ 0.65 (m, 6H), 1.11 (d, 2H, J=7.2), 1.3-1.6 (m, 3H), 2.3-2.4 (m, 4H), 2.68 (m, 3H), 3.00 (d, 2H, J=6.0), 4.0-4.5 (m, 5H), 7.0-7.3 (m, 14H);

$^{31}$P-NMR δ 19.6, 20.1 (two diastereomers of 1.2 : 1 ratio);

mass spectrum (FAB+) 713 (M+Li), 707 (MH+), 691, 663, 649, 607, 502, 457, 314, 318;

elemental analysis:

calculated for C$_{35}$H$_{41}$Li$_2$N$_4$O$_9$P: C, 59.49; H, 5.81; N, 7.93; P, 4.39. found: C, 59.27; H, 5.88; N, 7.90; P, 4.31.

EXAMPLE 2

Synthesis of Substrate II

A. Preparation of (-)N-(L-2-Hydroxy-4-methylpentanoyl)-L-alanine 4-Nitrobenzyl Amide A mixture of NHMPA (4.98 g, 24.5 mmol), 4-nitrobenzylamine hydrochloride (4.62 g, 24.5 mmol) and hydroxybenzotriazole (3.31 g, 24.5 mmol) was suspended in 80 mL of dry methylene chloride. Triethylamine (3.41 mL, 24.5 mmol) was added and the mixture was cooled to 0° C. and stirred under nitrogen. To this was added DCC (5.55 g, 27 mmol), and the resulting mixture was stirred with gradual warming to room temperature for 12h. The precipitated DCU was filtered off and the filtrate was concentrated in vacuo. To the residue was added ethyl acetate (120 mL), resulting in the precipitation of more DCU which was subsequently filtered off. The ethyl acetate was washed with water (2×40 mL), 3N HCl (40 mL), and saturated sodium bicarbonate (40 mL), then dried over MgSO$_4$ and concentrated to a white solid. Recrystallization from methylene chloride (60 mL) afforded a white crystalline solid (4.54 g, 13.5 mmol, 55% yield), identified as having the structural formula indicated above by the following analyses:

melting point 131°–132° C.;

IR (KBr pellet) 3318, 2945, 1659, 1616, 1553, 1526, 1352, 1147, 1102;

$^1$H-NMR (CDCl$_3$) δ 0.92 (d, 3H, J$_1$=6.6), 0.94 (d, 3H, J=6.6), 1.43 (d, 2H, J=5.1), 1.57 (m, 2H), 1.85 (m, 1H), 4.12 (m, 1H), 4.49 (d, 2H, J=6.0), 4.52 (m, 1H), 7.20 (d, 1H, J=7.4), 7.28 (m, 1H), 7.38 (d, 2H, J=8.7), 8.14 (d, 2H, J=8.7);

mass spectrum (EI) 337 (M), 322, 307, 301, 289, 281, 271, 263, 258, 250;

elemental analysis: calculated for C$_{16}$H$_{23}$N$_3$O$_5$: C, 56.97; H, 6.82; N, 12.46. found: C, 56.69; H, 6.88; N, 12.40.

B. Conversion to N-(t-Butoxycarbonyl)-phenylalanine Ester

Parallel syntheses for the D-isomer (R$^1$=H, R$^2$=benzyl) and L-isomer (R$^1$=benzyl, R$^2$=H) were performed. A description of the procedure used for each follows.

A mixture was prepared by combining N-(t-butoxycarbonyl)-phenylalanine (D or L) (0.608 g, 2.29 mmol), (−)N-(L-2-hydroxy-4-methylpentanoyl)-L-alanine 4-nitrobenzyl amide (0.77 g, 2.29 mmol) and hydroxybenzotriazole (0.31 g, 2.29 mmol) in dimethylformamide (10 mL). The mixture was cooled to 0° C. and stirred under nitrogen. To the mixture was added DCC (0.52 g, 2.5 mmol), and the mixture was stirred for 15h at 0° C. with gradual warming to room temperature. The DCU precipitate thus formed was filtered off and the solvent was removed in vacuo. The residue was dissolved in ethyl acetate to form more DCU which was subsequently filtered off. The ethyl acetate was treated as described in the preceding section of this Example. Silica gel chromatography using 1:1 ethyl acetate:hexanes afforded off-white solids (D: 0.45 g, 0.77 mmol, 34% yield; L: 0.62 g, 1.11 mmol, 48% yield), whose structures were confirmed as those of the isomers shown above as follows:

D-isomer melting point 118°–120° C.;

IR (KBr pellet) 3330, 2931, 2362, 2342, 1761, 1689, 1633, 1515, 1349, 1152;

$^1$H-NMR (CDCl$_3$) δ 0.75 (d, 3H, J=6.5), 0.82 (d, 3H, J=6.6), 1.34 (s, 9H), 1.50 (d, 3H, J=7.4), 1.62 (m, 3H), 2.98 (m, 2H), 4.22 (m, 1H), 4.50 (m, 2H), 4.89 (m, 1H), 4.99 (m, 1H), 7.01 (m, 1H), 7.15 (d, 1H, J=7.2), 7.32 (m, 5H), 7.41 (d, 2H, J=8.5 Hz), 8.17 (d, 2H, 8.7);

mass spectrum (FAB+) 585 (MH+), 529, 485, 433, 377;

elemental analysis: calculated for C$_{30}$H$_{40}$N$_4$O$_8$: C, 61.64; H, 6.85; N, 9.59. found: C, 61.59; H, 6.71; N, 9.60.

L-isomer melting point 116°–118° C.;

IR (KBr pellet) 3325, 2931, 2362, 2340, 1764, 1690, 1633, 1517, 1349, 1155;

$^1$H-NMR (CDCl$_3$) δ 0.90 (d, 6H, J=6.6), 1.42 (s, 9H), 1.50 (d, 3H, J=7.4), 1.70 (m, 3H), 3.05 (m, 2H), 4.22 (m, 1H), 4.50 (m, 2H), 4.89 (m, 1H), 4.99 (m, 1H), 7.01 (m, 1H), 7.15 (d, 1H, J=7.2), 7.32 (m, 5H), 7.41 (d, 2H, J=8.5 Hz), 8.17 (d, 2H, 8.7);

mass spectrum (FAB+) 585 (MH+), 529, 485, 433, 377;

elemental analysis: found: C, 61.66; H, 6.75; N, 9.61.

C. Preparation of N-(t-Butoxycarbonyl)-2-aminobenzoic Acid

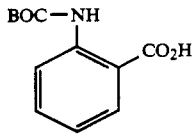

To a solution of diisopropylamine (3.85 mL, 27.5 mmol) in THF (100 mL) under nitrogen at −78° C. was added a 2.5M solution of n-butyllithium in hexanes (10 mL). To this mixture was added methylanthranilate (3.23 mL, 25 mmol) during continuous stirring of the mixture, followed by di-t-butyl dicarbonate (6.88 mL, 30 mmol). The mixture was allowed to warm to room temperature over 1h and was stirred for 24h, after which time the solvent was removed in vacuo. The residue was dissolved in methylene chloride (100 mL), and to the resulting solution was slowly added 1M sodium citrate/citric acid buffer, pH 4. The aqueous layer was extracted once with methylene chloride (70 mL). The combined organic layers were washed with the citrate buffer (100 mL), saturated NaHCO$_3$ (100 mL) and saturated NaCl (100 mL), dried over MgSO$_4$ and concentrated in vacuo. The methyl N-(t-butoxycarbonyl)anthranilate was purified by silica gel chromatography eluting with a gradient of 0 to 30% methylene chloride in hexanes. The product was hydrolyzed directly with 2N NaOH (14 mL) in methanol (10 mL) at 23° C. for 12h. Water (25 mL) and 1M citrate pH 4 (25 mL) were then added and the pH adjusted to 2.5 with concentrated HCl. The aqueous phase was extracted with methylene chloride (3×25 mL). The combined methylene chloride was dried over MgSO$_4$ and concentrated in vacuo to give pure N-(t-butoxycarbonyl)-2-aminobenzoic acid (2.49 g, 10.5 mmol, 38% yield) as a white solid, with structure confirmed as follows:

melting point 150°–152° C.;

IR (KBr pellet) 3321, 2988, 2362, 1733, 1673, 1588, 1532, 1420, 1258, 1152, 1047, 759;

$^1$H-NMR (CDCl$_3$) δ 1.55 (s, 9H), 7.04 (t, 1H, J=7.0), 7.57 (t, 1H, J=7.1 Hz), 8.10 (d, 1H, J=8.0 Hz), 8.47 (d, 1H, J=8.2 Hz), 10.05 (s, 1H);

elemental analysis: calculated for C$_{12}$H$_{15}$NO$_4$: C, 60.76; H, 6.33; N, 5.91; found: C, 60.69; H, 6.34; N, 5.88.

D. Conversion of the N-(t-Butoxycarbonyl)phenylalanine Ester to the N-(t-Butoxycarbonyl)-2-aminobenzoyl-phenylalanine Ester

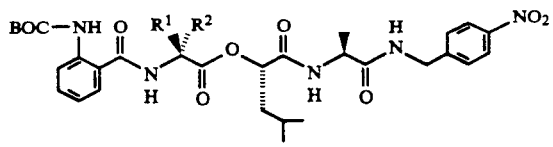

Parallel conversions of the D-isomer (R$^1$=H, R$^2$=benzyl) and L-isomer (R$^1$=benzyl, R$^2$=H) were performed. A description of the procedure used for each follows.

The t-butoxycarbonyl group of the N-(t-butoxycarbonyl)-2-aminobenzoylphenylalanine ester prepared in section B of this Example (450 mg, 0.77 mmol) was cleaved with TFA using the procedure described in Example 1, Section B above. The resulting TFA salt was combined with N-(t-butoxycarbonyl)-2-aminobenzoic acid (183 mg, 0.77 mmol), hydroxybenzotriazole (104 mg, 0.77 mmol), and triethylamine (0.32 mL, 2.3 mmol) in dry methylene chloride (10 mL). The mixture was stirred under nitrogen at 0° C. and DCC (175 mg, 0.85 mmol) was added. Stirring was continued for 12h at 0° C. with gradual warming to room temperature. The precipitated DCU was filtered off and the solvent removed in vacuo. The residue was dissolved in ethyl acetate to precipitate more DCU which was then filtered off. The ethyl acetate was washed with 5% citric acid (15 mL), saturated NaHCO$_3$ (15 mL), water (15 mL) and saturated NaCl (15 mL), then dried over MgSO$_4$ and concentrated in vacuo. The residue was purified by silica gel chromatography eluting with 1:1 ethyl acetate:hexanes to give the products as pale yellow solids (D-isomer: 240 mg, 0.34 mmol, 44% yield; L-isomer: 255 mg, 0.36 mmol, 47% yield). Verification of the structures as those of the formula shown above were as follows:

D-isomer melting point 85°–87° C.;

IR (KBr pellet) 3250 (br), 2931, 2855, 2348, 1736, 1660, 1631, 1582, 1455, 1398, 1345, 1251, 1166;

$^1$H-NMR (CDCl$_3$) δ 0.80 (d, 3H, J=6.5), 0.86 (d, 3H, J=6.6), 1.49 (s, 9H), 1.55 (d, 3H, J=7.3), 1.65 (m, 3H), 3.16 (m, 2H), 4.25 (m, 2H), 4.54 (m, 2H), 4.99 (m, 1H), 6.60 (d, 1H, J=2.1), 6.77 (t, 1H, J=3.2), 6.90 (t, 1H, 6.6 Hz), 7.1–7.3 (m, 5H), 7.46 (t, 1H, J=5.6), 7.87 (d, 2H, J=8.6), 8.31 (d, 2H, 8.5 Hz), 9.59 (s, 1H);

mass spectrum (FAB+) 704 (MH+), 604, 589, 452, 424, 381, 267, 239;

elemental analysis: calculated for C$_{37}$H$_{45}$N$_5$O$_9$ C., 63.16; H, 6.40; N, 9.96; found: C, 63.01; H, 6.40; N, 10.00.

L-isomer melting point 88°–90° C.;

IR (KBr pellet) 3250 (br), 2931, 2857, 2348, 1735, 1664, 1635, 1582, 1455, 1399, 1342, 1251, 1165;

$^1$H-NMR (CDCl$_3$) δ 0.84 (dd, 6H, J$_1$=6.4, J$_2$=4.6), 1.48 (s, 9H), 1.51 (d, 3H, J=7.3), 1.65 (m, 3H), 3.25 (m, 2H), 4.10 (m, 1H), 4.56 (m, 1H), 4.58 (m, 2H), 5.07 (m, 1H), 6.49 (d, 1H, J=2.1), 6.99 (t, 2H, J=5.6), 7.19 (d, 2H, J=7.6), 7.36 (t, 2H, J=6.1), 7.47 (m, 3H), 8.18 (d, 2H, J=6.9), 8.39 (d, 1H);

mass spectrum (FAB+) 704 (MH+), 604, 589, 452, 424, 381, 267, 239;

elemental analysis: found: C, 63.06; H, 6.44; N, 9.99.

E. Conversion to the 2-Aminobenzoylphenylalanine Ester (Enantiomers of Compound II)

In parallel reactions, the t-butoxycarbonyl group of each of the enantiomers produced in the preceding section (0.30 mmol) was removed with TFA using the procedure described in Example 1, Section B above. The TFA salt in ethyl acetate (1 mL) was neutralized with triethylamine (0.25 mL, 1.8 mmol) and purified by silica gel chromatography, eluting with 1:1 ethyl acetate: hexanes with 0.5% triethylamine to give the D-isomer (165 mg, 0.27 mmol, 91% yield) and the L-isomer (156 mg, 0.26 mmol, yield) as pale yellow crystalline solids. Structural verification was as follows:

D-isomer melting point 113°–114°C.;

IR (KBr pellet) 3361, 2966, 2368, 1743, 1673, 1631, 1525, 1349, 1265, 1167;

$^1$H-NMR (CDCl$_3$) 0.79 (d, 3H, J=6.5), 0.85 (d, 3H, J=6.6), 1.51 (d, 3H (m, 2H), 3.75 (s, 2H), 4.33 (m, 2H), 4.56 (m, 2H), 5.02 (m, 1H), 6.47 (s, 1H), 6.55 (t, 2H, J=8.2), 6.99 (t, 1H, J=2.j0), 7.1–7.4 (m, 6H) 7.56 (d, 1H, J=7.9), 7.91 (d, 2H, J=8.7);

mass spectrum (FAB+) 604 (MH+), 589, 572, 485, 452, 424, 391, 381;

elemental analysis: calculated for C$_{32}$H$_{37}$N$_5$O$_7$: C, 63.68; H, 6.14; N, 11.61;found: C, 63.60; H, 6.19; N, 11.55.

L-isomer melting point 116°–117° C.;

IR (KBr pellet) 3297, 2959, 1743, 1659, 1526, 1349, $^1$H-NMR (CDCl$_3$) 0.86 (d, 6H, J=6.4), 1.45 (d, 3H, J=7.3), 1.65 (m, 3H), 3.20 (m, 2H), 4.52 (m, 4H), 5.06 (t, 1H, J=6.5), 5.38 (s, 1H), 6.63 (d, 1H, J=2.2), 6.66 (m, 2H), 7.1–7.5 (m, 8H), 8.13 (d, 2H, J=6.9);

mass spectrum (FAB+) 604 (MH+), 589, 572, 485, 452, 424, 391, 381;

elemental analysis: found: C, 63.58: H, 6.14: N, 11.50.

EXAMPLE 3

Synthesis of the Tripeptide Substrate III

A. Preparation of N-(t-Butoxycarbonyl)-phenylalanyl-L-leucyl-L-alanine 4-Nitrobenzylamide

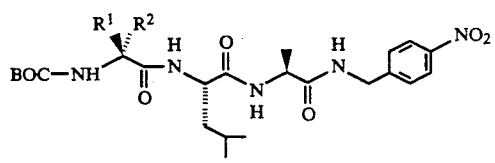

Parallel syntheses for the D-isomer (R$^1$=H, R$^2$=benzyl) and L-isomer (R$^1$=benzyl, R$^2$=H) were performed. The following procedure was used for each. The procedure of Example 2, Section B was followed, using t-butoxycarbonyl-D-phenylalanine for one isomer and t-butoxycarbonyl-L-phenylalanine for the other, and using L-leucyl-L-alanine 4-nitrobenzylamide of the formula

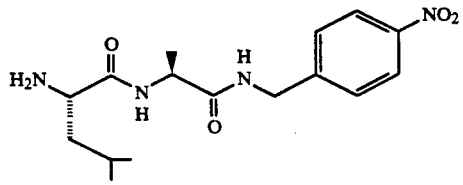

instead of (−)N-(L-2-hydroxy-4-methylpentanoyl)-L-alanine 4-nitrobenzyl amide. The reaction was carried out on a 2.0 mmol scale, using methylene chloride (10 mL) instead of dimethylformamide as the solvent. After the extractions, the crude product was purified by silica gel chromatography, eluting with 7:3 methylene chloride:ethyl acetate to afford the products as white solids (D-isomer: 0.83 g, 1.42 mmol, 71% yield; L-isomer: 0.77 g, 1.3 mmol, 62% yield). Verification of the structures was as follows:

D-isomer melting point 179°–180° C.;

IR (KBr pellet) 3290, 3086, 2960, 2368, 1658, 1525, 1349, 1251, 1167, 1019, 865, 705;

$^1$H-NMR (CDCl$_3$) δ 0.75 (d, 3H, J=6.4), 0.78 (d, 3H, J=6.5), 1.35 (s, 9H), 1.45 (d, 3H, J=7.3), 1.62 (m, 1H), 1.70 (m, 2H), 2.94 (m, 2H), 4.02 (m, 1H), 4.12 (m, 1H), 4.53 (m, 3H), 5.06 (d, 1H, J=4.6), 6.08 (d, 1H, J=3.8), 7.11 (d, 2H, J=6.5), 7.28 (m, 3H), 7.47 (d, 2H, J=8.4), 8.15 (d, 2H, J=8.7);

mass spectrum (FAB+) 584 (MH+), 484, 432, 376, 361, 337, 332, 305, 277, 266, 233, 224;

elemental analysis: calculated for C$_{30}$H$_{41}$N$_5$O$_7$: C, 61.75; H, 7.03; N, 12.01; found: C, 61.66; H, 7.17; N, 12.00.

L-isomer melting point 200°–202° C.;

IR (KBr pellet) 3290, 3071, 2966, 2368, 1666, 1525, 1341, 1267, 1170, 1019, 880, 709;

$^1$H-NMR (CDCl$_3$) δ 0.89 (d, 3H, J=5.9), 0.90 (d, 3H, J=6.0), 1.43 (s, 9H), 1.45 (d, 2H, J=7.3), 1.63 (m, 3H), 3.00 (m, 2H), 4.02 (m, 1H), 4.22 (m, 1H), 4.53 (m, 3H), 4.90 (s, 1H), 6.28 (d, 1H, J=3.8), 7.13 (d, 2H, J=6.5), 7.36 (m, 3H), 7.48 (d, 2H, J=8.7), 8.16 (d, 2H, J=8.7);

mass spectrum (FAB+) 584 (MH+), 484, 432, 376, 361, 337, 332, 305, 277, 266, 233, 224;

elemental analysis: found: C, 61.59; H, 7.11; N, 11.96.

B. Conversion to N-(t-Butoxycarbonyl)-2-aminobenzoyl-phenylalanyl-L-leucyl-L-alanine 4-Nitrobenzylamide

C. Conversion to 2-Aminobenzoylphenylalanyl-L-leucyl-L-alanine 4-Nitrobenzylamide (Enantiomers of Compound

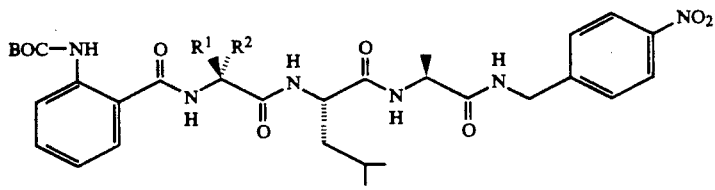

20

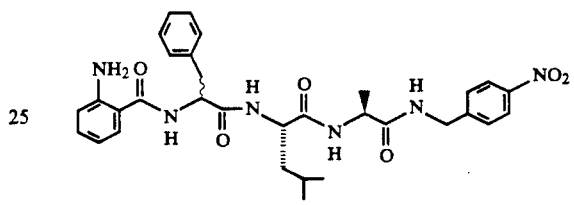

These compounds (D-isomer: R¹=H, R²=benzyl; L-isomer: R¹=benzyl, R²=H) were prepared according to the procedure of Example 2, Section D, starting however with the products of the preceding section of this Example, on a 0.90 mmol scale. Silica gel chromatography eluting with 7:3 methylene chloride:ethyl acetate for the D-isomer and 1:1 methylene chloride:ethyl acetate for the L-isomer. The products were isolated as white solids. The D-isomer weighed mg, 0.32 mmol, 36% yield; and the L-isomer weighed 182 mg, 0.26 mmol, 29% yield. Verification of product structures was as follows:

D-isomer melting point 111°–113° C.;

IR (KBr pellet) 3291, 2955, 2368, 1632, 1521, 1455, 1402, 1344, 1244, 1159, 1060, 1019, 752, 709;

$^1$H-NMR (CDCl$_3$) δ 0.78 (d, 3H, J=6.4), 0.83 (d, 3H, J=6.5), 1.42 (d, 3H, J=7.2), 1.48 (s, 9H), 1.64 (m, 3H), 3.10 (d, 2H, J=7.0), 4.24 (m, 1H), 4.31 (d, 2H, J=5.9), 4.5–4.6 (m, 2H), 6.47 (m, 1H), 6.80 (m, 1H), 6.95 (t, 1H, J=6.2), 7.2–7.4 (m, 6H), 7.50 (t, 1H, J=6.2), 7.93 (d, 2H, J=8.7), 8.35 (d, 1H, J=8.8), 9.82 (s, 1H);

mass spectrum (FAB+) 703 (MH+), 603, 580, 551, 480, 451, 380, 367, 357, 337, 267, 239.

elemental analysis: calculated for C$_{37}$H$_{46}$N$_6$O$_8$: C, 63.25; H, 6.55; N, 11.97; found: C, 63.11; H, 6.50; N, 12.19.

L-isomer melting point 175°–177° C.;

IR (KBr pellet) 3290, 2966, 2368, 1645, 1526, 1455, 1406, 1349, 1244, 1159, 1050, 1019, 752, 708;

$^1$H-NMR (CDCl$_3$) δ 0.89 (d, 3H, J=5.9), 0.90 (d, 3H, J=6.0), 1.49 (s, 9H), 1.50 (d, 3H, J=7.3), 1.65 (m, 3H), 3.15 (m, 2H), 4.40 (m, 1H), 4.54 (m, 4H), 6.60 (m, 1H), 6.76 (m, 1H), 6.98 (t, 1H, J=6.2), 7.2–7.4 (m, 6H), 7.48 (d, 1H, J=6.5), 8.15 (d, 2H, J=8.5) 8.4), 9.75 (s, 1H);

mass spectrum (FAB+) 703 (MH+), 603, 580, 551, 480, 451, 380, 367, 357, 337, 267, 239;

elemental analysis: found: C, 63.08; H, 6.52; N, 12.10.

These compounds were prepared individually by treatment of the two enantiomers formed in the preceding section of this example (140 mg, 0.20 mmol) with TFA as described above in Example 1, Section B. Silica gel chromatography eluting with ethyl acetate containing 2% methanol and 0.4% triethylamine gave off-white solids for each product (D-isomer: 115 mg, 0.191 mmol, 95% yield; L-isomer: 110 mg, 0.183 mmol, 91% yield). Verification of the structures was as follows:

D-isomer melting point 180°–182° C.;

IR (KBr pellet) 3135, 1680, 1560, 1462, 1398, 1216, 1152, 857, 805, 723;

$^1$H-NMR (acetone-d$_6$) δ 0.73 (d, 3H, J=6.6), 0.77 (d, 3H, J=6.6), 1.36 (d, 3H, J=7.4), 1.50 (m, 3H), 3.15 (m, 2H), 4.05 (m, 1H), 4.31 (m, 3H), 4.50 (m, 1H), 6.10 (s, 1H), 6.48 (t, 1H, J=6.2), 6.72 (d, 1H, J=8.1), 7.15 (t, 1H, J=6.2), 7.26 (m, 3H), 7.40 (t, 2H, J=7.3), 7.67 (m, 2H), 7.82 (m, 1H), 7.96 (m, 2H);

mass spectrum (FAB+) 603 (MH+), 451, 433, 380, 337, 267, 245, 239;

elemental analysis:
calculated for C$_{32}$H$_{38}$N$_6$O$_6$: C, 63.79; H, 6.31; N, 13.95; found: C, 63.88; H, 6.41; N, 13.69.

L-isomer melting point 183°–185° C.;

IR (KBr pellet) 3290, 2953, 1645, 1526, 1398, 1349, 1258, 1157, 752, 704;

$^1$H-NMR (acetone-d$_6$) 6 0.82 (d, 3H, J=6.4), 0.88 (d, 3H, J=6.5), 1.62 (d, 3H, J=7.4), 1.69 (m, 3H), 3.20 (m, 2H), 4.12 (m, 1H), 4.3–4.5 (m, 3H), 4.60 (m, 1H), 6.63 (d, 1H, J=8.1), 6.77 (t, 1H, J=7.2), 7.2–7.4 (m, 6H), 7.60 (d, 1H, J=7.2), 7.67 (d, 1H, J=7.2 Hz), 7.87 (d, 2H, J=8.7), 8.15 (m, 1H);

mass spectrum (FAB+) 603 (MH+), 451, 433, 380, 337, 307, 277, 267.

elemental analysis: found: C; 63.92; H, 6.44; N, 13.77.

EXAMPLE IV

Synthesis of Substrate IV

A. Preparation of N-(t-Butoxycarbonyl)-D-leucine Ester of (−)N-(L-2-Hydroxy-4-methylpentanoyl)-L-alanine 4-Nitrobenzyl Amide

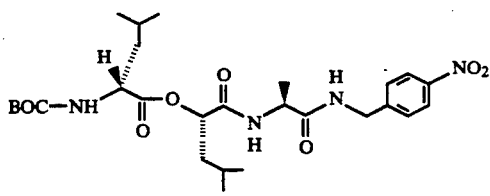

The procedure of Example 2, Section B was followed, using N-(t-butoxycarbonyl)-D-leucine in place of the N-(t-butoxycarbonyl)-phenylalanines, on a 2.0 mmol scale. The elution solvent was 2% methanol in methylene chloride in silica gel chromatography to give a white solid (550 mg, 1.0 mmol, 50% yield). The structure was verified as that of the above formula as follows:

melting point 87°–88° C.;

IR (KBr pellet) 3304, 2966, 2355, 1673, 1526, 1349, 1251, 1167, 857;

$^1$H-NMR (CDCl$_3$) δ 0.95 (m, 12H), 1.34 (s, 9H), 1.52 (d, 3H, J=7.3 Hz), 1.62 (m, 4H), 1.80 (m, 2H), 4.05 (m, 1H), 4.40 (m, 1H), 4.55 (m, 2H), 4.94 (m, 1H), 7.00 (s, 1H), 7.41 (d, 2H, J=8.7), 8.17 (d, 2H, J=8.7);

mass spectrum (FAB+) 599 (MH+), 399;

elemental analysis: calculated for $C_{27}H_{42}N_4O_8$: C, 58.91; H, 7.64; N, 10.18; found: C, 59.09; H, 7.70; N, 10.13.

B. Conversion to N-(t-Butoxycarbonyl)-aminobenzoyl-D-leucine Ester

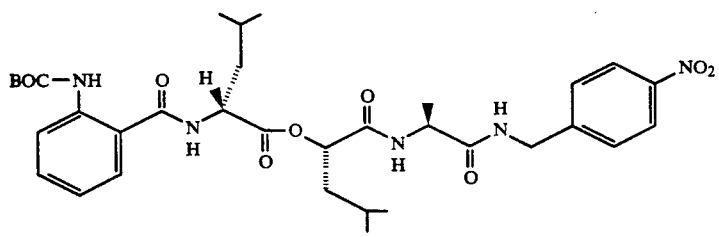

The procedure of Example 1, Section D was followed, using the N-(t-butoxycarbonyl)-D-leucine ester as the starting material, on a 0.73 mmol scale. The product was not characterized at this stage, but instead used directly in the following cleavage reaction.

C. Removal of t-Butoxycarbonyl Group

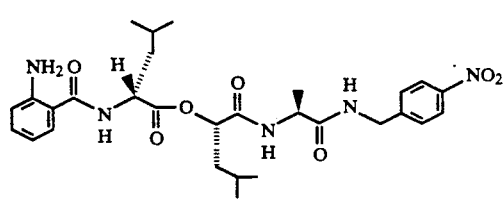

The t-butoxycarbonyl group was cleaved from the ester with TFA by the procedure described in Example 1, Section B above. The crude product was purified by silica gel chromatography, eluting with a gradient of 0 to 2.5% methanol in methylene chloride containing 0.5% triethylamine to give an off-white crystalline solid (250 mg, 0.44 mmol, 60% yield), whose structure was verified as that of the formula above as follows:

melting point 78°–80° C.;

IR (KBr pellet) 3331, 2932, 2368, 1722, 1663, 1526, 1406, 1350, 1167, 864;

$^1$H-NMR (CDCl$_3$) δ 0.99 (m, 12H), 1.49 (d, 2H, J=7.3), 1.71 (m, 4H), 1.93 (m, 2H), 3.50 (m, 1H), 4.07 (m, 1H), 4.3–4.6 (m, 3H), 5.08 (m, 1H), 6.73 (m, 1H), 6.82 (d, 1H, J=6.8), 7.02 (m, 1H), 7.20 (t, 1H, J=6.9), 7.38 (d, 2H, J=8.7), 8.16 (d, 2H, J=8.7);

mass spectrum (FAB+) 570 (MH+), 547, 531, 395, 373, 367, 347;

elemental analysis: calculated for $C_{29}H_{39}N_5O_7$: C, 61.16; H, 6.85; N, 12.30; found: C, 61.17; H, 6.88; N, 12.22.

EXAMPLE 5

Synthesis of Substrate V

A. Preparation of N-(t-Butoxycarbonyl)-D-tryptophan Ester of (-)N-(L-2-Hydroxy-4-methylpentanoyl)-L-alanine 4-Nitrobenzylamide

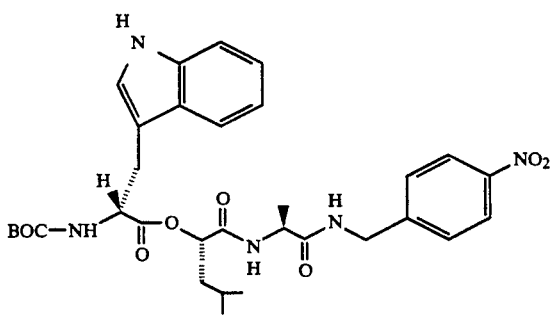

The procedure of Example 2, Section B was followed, using N-(t-butoxycarbonyl)-D-tryptophan in place of the N-(t-butoxycarbonyl)-phenylalanines, on a 2.0 mmol scale. The elution solvent was 2% methanol in methylene chloride in silica gel chromatography to give a crystalline yellow solid (970 mg, 1.56 mmol, 78% yield). The structure was verified as that of the above formula as follows:

melting point 93°–95° C.;

IR (KBr pellet) 3311, 2938, 2355, 1673, 1526, 1393, 1349, 1250, 1159, 748;

¹H-NMR (CDCl₃) δ 0.71 (d, 3H, J=6.6), 0.74 (d, 3H, J=6.7), 1.33 (s, 9H), 1.49 (d, 3H, J=7.3), 1.61 (m, 3H), 3.18 (m, 2H), 4.50 (m, 3H), 4.85(m, 1H), 5.02 (m, 1H), 7.02 (s, 1H), 7.20 (m, 2H), 7.42 (m, 3H), 8.17 (d, 2H, J=8.7);

mass spectrum (FAB+) 623 (MH+), 568, 524, 506, 493, 416, 393;

elemental analysis: calculated for C₃₂H₄₁N₅O₈: C, 61.64; H, 6.58; N, 11.23; found: C, 61.86; H, 6.78; N, 11.11.

B. Conversion to N-(t-Butoxycarbonyl)-aminobenzoyl-D-tryptophan Ester

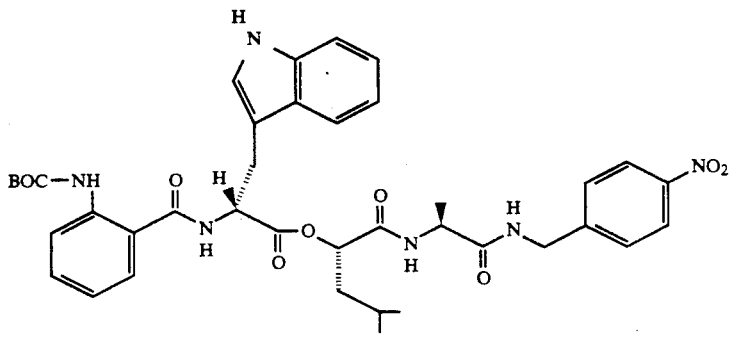

The procedure of Example 1, Section D was followed, using the N-(t-butoxycarbonyl)-D-tryptophan ester as the starting material, on a 0.80 mmol scale. The product was not characterized at this stage, but instead used directly in the following cleavage reaction.

C. Removal of t-Butoxycarbonyl Group

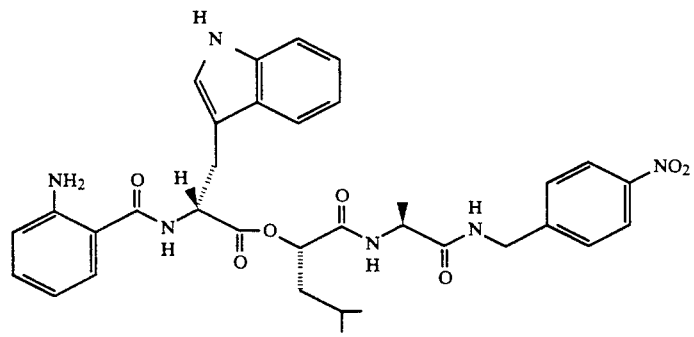

The t-butoxycarbonyl group was cleaved from the ester with TFA by the procedure described in Example 1, Section B above. The crude product was purified by silica gel chromatography, eluting with a gradient of 0 to 2.5% methanol in methylene chloride containing 0.5% triethylamine to give a crystalline yellow solid (300 mg, 0.47 mmol, 58% yield), whose structure was verified as that of the formula above as follows:

melting point 80°–82° C.;

IR (KBr pellet) 3396, 3114, 2945, 2362, 1665, 1526, 1398, 1349, 1223, 1167, 864, 744:

¹H-NMR (CDCl₃) δ 0.78 (d, 3H, J=6.5), 0.80 (d, 3H, J=6.4), 1.51 (d, 3H, J=7.3), 1.65 (m, 3H), 3.30 (m, 2H), 4.05 (m, 1H), 4.50 (m, 3H), 5.01 (m, 1H), 6.6–7.0 (m, 4H), 7.22 (m, 2H), 7.41 (m, 3H), 7.53 (m, 1H), 8.17 (d, 2H, J=8.7), 8.40 (m, 1H):

mass spectrum (FAB+) 643 (MH+), 620, 506, 339, 311;

elemental analysis: calculated for C₃₄H₃₈N₆O₇: C, 63.55; H, 5.92; N, 13.08; found: C, 63.67; H, 5.98; N, 13.00.

EXAMPLE 6

Antibody Generation and use in Hydrolysis Reactions

The hapten I (i.e., the mixture of diastereomers) was coupled via its carboxylic acid moiety to the carrier protein keyhole limpet hemocyanin by conventional techniques, and the conjugate was used to elicit an immune response in Swiss Webster mice. Monoclonal antibodies were then generated by standard methods of fusion using SP2/0 myeloma as a fusion partner. The procedure is described by Urnovitz, H. B., et al., J. Immunol. 140:558 (1988). As is evident from its formula, the hapten contains analogs of fluorogenic groups which allow hydrolysis of the substrates II and III to be monitored by observing the fluorescence increase which occurs when the fluorescent 2-aminobenzoyl group is separated from the quenching 4-nitrobenzylamide in the reaction, as described by Nishino, N., et al., J. Biol. Chem. 255:3482 (1980).

The IgG's were purified from ascites fluid by affinity chromatography using protein A coupled Sepharose 4B, according to the procedure of Kronvall, G., et al., J. Biol. Chem. 105:1116 (1970), followed by Pharmacia Mono Q 10/10 anion exchange chromatography using a linear gradient of 85 mM to 150 mM sodium chloride (20 mM Tris, pH 7.8) over twenty minutes (flow rate of 4.0 mL/min). The antibody-containing fractions were dialyzed exhaustively against assay buffer and judged to be homogeneous by 12.5% sodium dodecyl sulfate polyacrylamide gel electrophoresis with Coomasie blue staining, according to Laemmli, V., Nature (London) 227:680 (1970).

Of the various IgG's isolated and cloned, thirty-one were found to be specific for the hapten. Hydrolysis reactions were conducted by adding a stock solution (in dimethylsulfoxide) of the candidate substrate (5 μL) to the 3.33 μL of the antibody in 0.5 mL of reaction buffer, which was 0.2M borate, 0.15M sodium chloride (BBS), pH 8.0, at 24 C. Ester hydrolysis was monitored by fluorescence measurement with a Perkin-Elmer LS 5B spectrophotometer using 340 nm for excitation and 415 nm for emission. Fluorescence values for hydrolysis were calibrated by alkaline hydrolysis at pH 12, by addition of 10 μL of 7N NaOH to the reaction mixture, followed by adjustment of the pH to assay conditions with 12N HCl and correcting for dilution. The fluorescence changes upon complete hydrolysis showed a consistent linear dependence on substrate concentration up to 50 μM of substrate. Protein molarity was determined from $A_{280}$ ($E_1cm^{0.1\%} = 1.37$) and a molecular weight of 150,000 for IgG.

None of the thirty-one IgG's specific for the hapten accelerated the hydrolysis of the tripeptide III to a measurable extent, when tested under a variety of conditions. Similar tests conducted with the esters IV and V were likewise unsuccessful.

Eighteen of the antibodies, however, did catalyze the hydrolysis of the ester II. All of the eighteen were selective for the D-phenylalanine-containing diastereomer, however, despite the fact that the hapten used to generate the antibodies was itself a mixture of diastereomers.

Of these eighteen, five were selected for further study. To detect for saturation kinetics and competitive inhibition by the hapten, Eadie-Hofstee and Dixon plots, according to Dowd, J. E., et al., *J. Biol. Chem.* 146:85 (1942) and Dixon, G., *Biochem. J.* 55:170 (1953), were generated for each of the five. The results are shown in the following table.

TABLE

| IgG | $k_{cat}^{(a)}$ (min$^{-1}$ × 10$^{-3}$) | $K_m^{(a)}$ (μM) | $K_i^{(b)}$ (μM) | $k_{cat}/\{k_{OH-}(OH^-)\}$ | $k_L/k_D$ |
|---|---|---|---|---|---|
| 6E4D5 | 2.3 ± 0.3 | 4.4 ± 0.5 | 0.5 ± 0.1 | 33 | <0.005 |
| 3E10D8 | 7.0 ± 0.7 | 6.0 ± 0.6 | 0.8 ± 0.2 | 100 | 0.025 |
| 3E9F2D10 | 5.8 ± 0.6 | 4.5 ± 0.5 | 1.6 ± 0.4 | 83 | 0.018 |
| 2H12E4 | 18.7 ± 2.0 | 14.8 ± 1.0 | 2.4 ± 0.6 | 267 | 0.005 |
| 2B5B11 | 9.8 ± 1.0 | 6.2 ± 0.6 | 1.4 ± 0.3 | 140 | <0.005 |

$^{(a)}$For ester II, D-isomer
$^{(b)}$For hapten I

With all five antibodies, multiple (i.e., more than ten) turnovers were observed with no loss of catalytic activity. In the table, the rate enhancements $k_{cat}/\{k_{OH-}(OH^-)\}$ are derived from $k_{cat}$ and $k_{OH-}(OH^-)$ for the hydrolysis of the ester II (D-isomer). The rate $v_{uncat} = k_{OH-}(D-II)(OH^-)$ was comp directly to the rate of hydrolysis in the IgG-substrate complex, $v_{complex} = k_{complex}(complex)(OH^-)$. The value of the pseudo-first order rate constant $k_{OH-}(OH^-)$ was determined to be $(7.0 \pm 0.2) \times 10^{-5}$ min$^{-1}$ at 24° C., pH 8.0, by extrapolation of the rate of the uncatalyzed reaction to zero buffer concentration.

As the data in the table indicates, the antibody-catalyzed reaction shows a high degree of stereospecificity for the D-phenylalanine-containing isomer of ester II. With all five of the antibodies studied, hydrolysis of the L-phenylalanine-containing isomer was catalyzed at <2.5% the rate of the D-phenylalanine-containing isomer, based on initial rates. With three of the five antibodies, in fact, the ratio of hydrolysis rates was less than 0.5%, which was the limit of detection due to the background hydrolysis rate at pH 8.0. Similarly, no hydrolysis was indicated for the esters IV and V, for which the rate ratios corresponding to those in the last column of the table were both <0.005 at 30 μM substrates, pH 8.0, 24° C.

The rates of hydrolysis were measured at ten different pH values between pH 7 and 10, in BBS, at 24° C., with 50 μM ester II (D-isomer) (approximately $V_{max}$ conditions). Plots of the resulting data indicated that the catalytic activity of the antibodies 6E4D5, 2H12E4 and 2B5B11 showed a linear dependence on hydroxide ion concentration with a slope of log $v_{obs}$ vs. pH of 0.82 ± 0.05 throuqhout this ranqe. The antibodies 3E10Ds and 3E9F2D10 showed an inflection at pH 9.2, with the same slope up to the inflection point, where the rate levelled off. This result suggests the presence of a catalytic amino acid side chain in these two antibodies, the side chain being one such as a tyrosine residue, which could act as a nucleophile, producing a labile tyrosine-ester intermediate.

To test the importance of the tyrosine residues, the antibodies (20 μM) were treated to modify the tyrosine residues. BBS, pH 8, for 1h at 25° C., followed by dialysis against BBS, according to the procedure described by Sokolovsky, M., et al., *Biochemistry* 5:3582 (1966). The result was the destruction of catalytic activity in all of the antibodies. In separate experiments, the hapten I was present in the reaction mixture at 250 μM. Greater than 90% of the catalytic activity was retained in these latter experiments.

The foregoing is offered primarily for purposes of illustration. It will be readily apparent to those skilled in the art that further modifications, substitutions, and variations of various kinds may be made without departing from the spirit and scope of the invention.

What is claimed is:

1. A method for the production of an optically active carboxylic acid by stereospecific hydrolysis of an ester at a preselected —$CO_2$—group thereof, said ester having a chiral center on the acid portion thereof and said ester being present in a mixture of D- and L-diastereomers defined by a difference in configuration at said chiral center on said acid portion of said ester, said method comprising:
  (a) contacting said D- and L-ester diastereomer mixture with antibody elicited by a mixture of antigen diastereomers which are stable analogs of unstable transition states of said ester diastereomers tending to decompose by cleaving at said preselected —$CO_2$—group to form hydrolysis products thereof, said antibody being one which promotes said hydrolysis; and
  (b) recovering said optically active carboxylic acid from said hydrolysis products, such that a preponderance of said optically active carboxylic acid is the D-siomer thereof.

2. A method in accordance with claim 1 in which said chiral center is a carbon atom located at a distance from the carbon atom of said preselected —CO$_2$—group by four atoms or less.

3. A method in accordance with claim 1 in which said chiral center is a carbon atom located at a distance from the carbon of said preselected —CO$_2$—group by two atoms or less.

4. A method in accordance with claim 1 in which said chiral center is a carbon atom adjacent to the carbon of said preselected —CO$_2$—group.

5. A method in accordance with claim 4 in which said ester is an ester of a carboxylic acid selected from the group consisting of alkyl and aryl carboxylic acids, said ester diastereomer mixture is defined as a mixture of D- and L-configurations at said chiral center on said acid portion of said ester, and said optically active carboxylic acid recovered in step (b) is a D-enantiomer of said carboxylic acid.

6. A method in accordance with claim 4 in which said ester is an ester of an amino acid, said ester diastereomer mixture is a mixture of D- and L-configurations at said chiral center on said acid portion of said amino acid ester, and said optically active carboxylic acid recovered in step (b) is a D-enantiomer of said amino acid.

7. A method in accordance with claim 4 in which said ester is an ester of an acyclic carboxylic acid, said ester diastereomer mixture is a mixture of D- and L-configurations at said chiral center on said acid portion of said ester, and said optically active carboxylic acid recovered in step (b) is a D-enantiomer of said acyclic carboxylic acid.

8. A method in accordance with claim 4 in which said ester is an ester of a heterocyclic carboxylic acid, said ester diastereomer mixture is a mixture of D- and L-configurations at said chiral center on said acid portion of said ester, and said optically active carboxylic acid recovered in step (b) is a D-enantiomer of said heterocyclic carboxylic acid.

9. A method in accordance with claim 1 in which each of said antigen diastereomers is an analog of said ester diastereomers with a corresponding member selected from the group consisting of

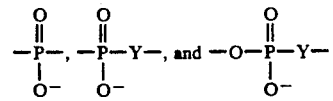

where Y is O or S, substituting for said preselected —CO$_2$—group.

10. A method in accordance with claim 1 in which each of said antigen diastereomers is a phosphonate analog of said ester diastereomers with the group

substituting for said preselected —CO$_2$—group.

11. A method in accordance with claim 1 in which each of said antigen diastereomers is a hydroxymethylene analog of said ester diastereomers with the group

substituting for said preselected —CO$_2$—group.

12. A method in accordance with claim 1 in which each of said antigen diastereomers is an analog of said ester diastereomers with a member selected from the group consisting of

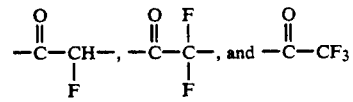

substituting for said preselected —CO$_2$—group.

13. A method in accordance with claim 1 in which said ester is a member selected from the group consisting of alkyl and substituted alkyl esters of amino acids.

14. A method in accordance with claim 1 in which said ester is a peptide-substituted alkyl ester of an amino acid.

15. A method in accordance with claim 1 in which said ester is an oligopeptide-substituted alkyl ester of an amino acid.

16. A method in accordance with claim 1 in which said antibody is monocolnal antibody.

17. A method in accordance with claim 4 in which said ester is an ester of a substituted phenylalanine, said ester enantiomer mixture is a mixture of D- and L-isomers of said substituted phenylalanine ester, and said optically active carboxylic acid recovered in step (b) is a D-isomer of said substituted phenylalanine.

* * * * *